Figure 1:
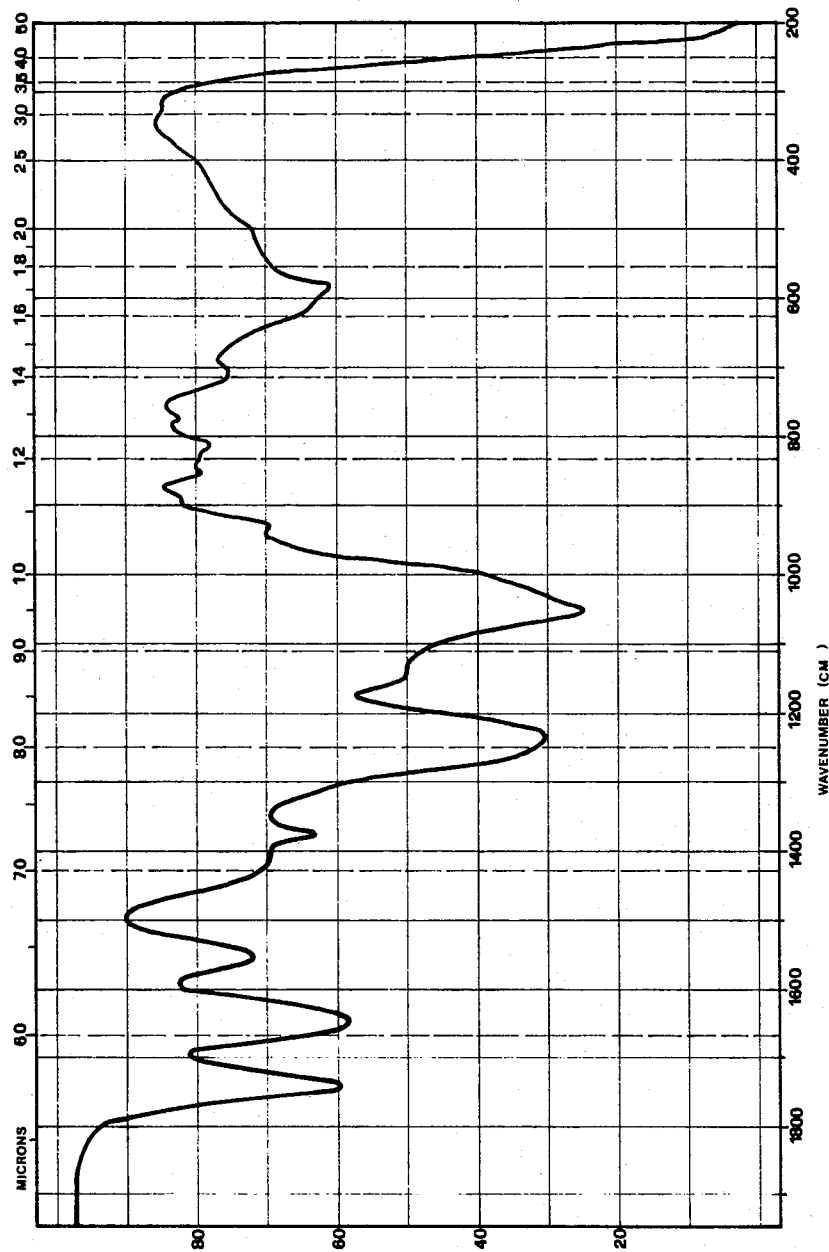

United States Patent [19]

Fedeli

[11] Patent Number: 4,489,066
[45] Date of Patent: Dec. 18, 1984

[54] ARTERIAL POLYSACCHARIDE COMPLEX, A METHOD FOR ITS PREPARATION AND COMPOSITION COMPRISING SAME

[75] Inventor: Gianfranco Fedeli, Milan, Italy

[73] Assignee: Mediolanum Farmaceutici S.r.L., Milan, Italy

[21] Appl. No.: 877,700

[22] Filed: Jul. 10, 1978

[30] Foreign Application Priority Data

Feb. 14, 1977 [IT]  Italy .......................................... 20261

[51] Int. Cl.³ ...................... A61K 31/73; C08B 37/00; C07H 5/06
[52] U.S. Cl. .................................. 424/181; 435/104; 536/21; 536/114; 536/1.1; 536/18.1
[58] Field of Search ....................... 536/114, 1, 21, 53, 536/181, 18; 424/181

[56] References Cited

U.S. PATENT DOCUMENTS

| | | | |
|---|---|---|---|
| 3,201,312 | 8/1965 | Bucourt | 536/21 |
| 3,210,250 | 10/1965 | Bucourt | 536/21 |
| 3,232,838 | 1/1966 | Nomine et al. | 536/21 |
| 3,506,642 | 4/1970 | Koh et al. | 536/21 |
| 3,585,184 | 6/1971 | Wolfrom et al. | 536/1 |
| 3,754,925 | 8/1973 | Kimura et al. | 536/1 |

Primary Examiner—Johnnie R. Brown
Attorney, Agent, or Firm—Farrell R. Werbow

[57] ABSTRACT

An arterial polysaccharide complex of anionic character consisting of hexosamine glycanmonosulphates (FAPA) derived from the aorta of young mammals and a process for its preparation.

7 Claims, 1 Drawing Figure

ARTERIAL POLYSACCHARIDE COMPLEX, A METHOD FOR ITS PREPARATION AND COMPOSITION COMPRISING SAME

This invention relates to a new polysaccharide complex produced by extraction from the aorta of young mammals, and its use in the treatment of arteriopathies and conditions associated therewith.

BACKGROUND

In recent years, numerous drugs have been proposed for aiding the return to normal concentrations of the various lipid components of the serum, in consideration of the particular seriousness of hyperlipidemias and dislipidemias in the etiopathogenesis of numerous illnesses, including illnesses of social interest. These drugs can be distinguished schematically in the following manner by their action mechanism:

(1) those which inhibit the intestinal absorption of cholesterol;
(2) those which act on the secretion of bile acids;
(3) those which inhibit the synthesis of cholesterol and the mobility of the fatty acids of the adipose tissue;
(4) those which activate fibronolysis and thrombolysis; and
(5) those which favor increase in the removal of lipoproteins.

Among these latter drugs, heparin and analogous substances generally known as heparinoids have assumed special importance in the treatment of hyperlipidemias and dislipidemias.

Among the various pharmacological actions of heparin, one of particular importance is the so-called clarifying action which consists essentially of inducing the appearance in the bloodstream of lipoproteinlipase, a physiological enzyme which separates the ester bonds of triglycerides to transform them into monoglycerides and free fatty acids. This action is entirely independent of the anticoagulating action, which represents the negative side and determines the limit of use of heparin in this type of therapy.

Again, within the field of antiarteriosclerotic therapy, it has been stated in published works (Comi and Coll., Boll, Chim. Farm. 106/5/309/21 (1967); French Pat. No. M 4,871filed Nov. 24, 1965) that by administering total aorta extracts to rabbits which have been made hypercholesterolemic by means of chloresterol-base diets, a strong reduction in atheromatosis formations have been obtained. On the other hand, it has been shown (Dall'Occhi and Coll. Adv. Exi. Med. Biol. 1967 1,468/83) that the total aorta extract leads to reactions of immunity with harmful effects on the pulmonary arteries.

THE INVENTION

We have now discovered a new and specific polysaccharide complex of anionic character which has demonstrated suprising antiarteriosclerotic properties in addition to a complete lack of side-effects.

Also, this invention relates to a means for extracting said polysaccharide complex from the aorta of young mammals.

This new complex, which for simplicity will be indicated hereinafter by the letters FAPA (Arterial Antiarteriosclerotic Polysaccharide Factor), is characterized unambiguously by the following chemical-physical properties:

(a) On hydrolysis FAPA liberates hexosamine, uronic acids and sulphates in the molar ratios of approximately 1/1/1 with variable quantities of nucleosides.

After acid hydrolysis of the FAPA, analysis shows the following average composition of the polysaccharide components.

(1) Hexosamine (glucosamine): specific colorimetric reaction of the amine in hexoses with p-dimethylaminobenzaldehyde: 30±2.25%
(2) Uronic acid: specific colorimetric reaction with carbazole: 30.5±%
(3) Organic Sulphate ($SO_4$): in accordance with FU 8th Ed. Vol. I, page 106, paragraph B: 16.5±3%
(4) Sodium (NA): determined by atomic absorption (not routine): 10±2%
(5) Ash: 15±3%

(b) Electrophoretically, FAPA separates into three anionic bands distinguishable with Alcian Blau and Toluidine Blue.

The following table shows the relative electrophoretic mobility of the three anionic bands.

| Band | Anodic Mobility | Average Densitometric Ratios of Positive Toluidine Blue Bands |
|---|---|---|
| 1 | U: 2.2 ± 0.5 · $10^{-4} cm^2 V^{-1} sec.^1$ | 14 ± 3% |
| 2 | U: 2.09 ± 0.5 · $10^{-4} cm^2 V^{-1} sec.^1$ | 9 ± 2% |
| 3 | U: 1.93 ± 0.05 · $10^{-4} cm^2 V^{-1} sec.^1$ | 77 ± 8% |

(c) FAPA reacts with alkaline and alkaline earth metals to form salts which are very soluble in water, whereas the salts which it forms with the aliphatic ammonium ion are insoluble.

(d) The sodium salt is 2% soluble in 50% ethyl alcohol, whereas, the acid form is 2% soluble in 70% ethyl alcohol.

(e) FAPA reacts with Toluidine Blue to give a minimum metachromatic reaction (approximately 1/10 of that given by heparin).

(f) Spectrophotometrically, it shows a maximum of 260±1 nm.

(g) FAPA shows a rotatory power on polarised light of −11° to −22°.

(h) The infrared spectrum of the substance determined in KBr, to which the graph of FIG. 1 refers, shows the following functions:

—COOH

—NHR

—COCH$_3$

—OSO$_3$H

—CH$_2$OH

From the total analytical data it can be established that FAPA has the following structure:

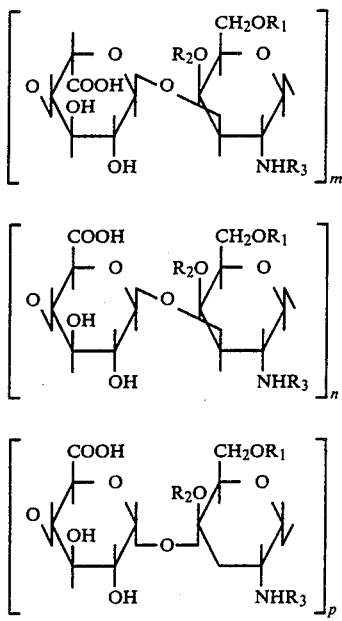

wherein $R_1$ and $R_2$ are —H or $SO_3H$, $R_3$ is —$SO_3H$ or —CO—$CH_3$, and m, n, p are whole numbers which can vary over a wide range and define a molecular weight of 10,000 to 30,000 daltons for the polysaccharide chains.

These characteristics, and in particular the molecular ratios of the components obtained after hydrolysis, indicate that FAPA may be defined chemically as a molecular complex consisting of hexosaminglycanmonosulphates (chondroitin sulphates B and C and heparitin sulphates of the arterial wall).

The process for producing FAPA according to the present invention is characterized essentially by the following operations:

(1) removing and immediately grinding the aortas of young mammals which have just been slaughtered;
(2) homogenising and suspending said tissues in water or suitable saline solutions;
(3) attack by proteolytic enzymes such as trypsin, chymotrypsin, pancreatin, papain, ficin or bromelin, under the respective optimum pH, temperature and time conditions;
(4) separating the digested liquid by filtration and collecting same;
(5) precipitating FAPA from the digested liquid by solvents miscible with water and/or by forming insoluble salts with the aliphatic ammonium ion; and
(6) purifying by salification with alkaline or alkaline earth metal bases, decolouration with permanganate, treatment with alkali at 70° C. for eliminating the terminal parts of the residual peptide chains, separation of the desired salt form with solvents (sodium, potassium, calcium salts, etc.), filtration, sterilization and lyophilisation.

The pharmacological properties of FAPA have been examined in comparison with certain antiarteriosclerotic preparations of the aforesaid type; in particular it has been examined in comparison with heparin, the clarifying drug for amutonomasia, and with the total aorta extract.

The following basic characteristics were determined by in vivo experimentation:

(1) Action of experimental arteriosclerosis

This study was carried out on rabbits divided into batches of five animales each fed with heterogenous diet rich in cholesterol.

The blood of the animals was tested for determining the esterified fatty acids (EFA), the total cholesterol, the betalipoproteins and the coagulation time. The cholesterol content of the aortic tissue was determined, together with the incidence of atheromas. Table I summarises the results obtained using FAPA, heparin and total aorta extract, after 40 days of treatment.

TABLE I

|  | EFA mg/100 ml of serum | Cholesterol mg/100 ml of serum | B-lipoproteins mg/100 ml of serum | coag. time log. of minutes | aort. cholesterol mg/100 g of dry substance | atheromas |
|---|---|---|---|---|---|---|
| controls | 456 ± 14 | 215 ± 19 | 78 ± 4 | 0.78 ± 0.06 | 2.85 ± 0.12 | + + + + |
| FAPA 1 mg/kg | 180 ± 5 | 90 ± 15 | 40 ± 2.5 | 0.81 ± 0.04 | 1.98 ± 0.08 | + + |
| FAPA 10 mg/kg | 162 ± 8 | 76 ± 13 | 35 ± 13 | 0.9 ± 0.04 | 1.7 ± 0.04 | + |
| Heparin 1 mg/kg | 171 ± 11 | 78 ± 13 | 38 ± 1 | 1.9 ± 0.4 | 2 ± 0.05 | + |
| Heparin 10 mg/kg | 138 ± 8 | 76 ± 15 | 30 ± 2 | 2.3 ± 0.8 | 1.8 ± 0.03 | + |
| Total aorta extract 1 mg/kg | 430 ± 14 | 190 ± 14 | 79 ± 3 | 0.75 ± 0.1 | 2.9 ± 0.2 | + + + + |
| Total aorta extract 10 mg/kg | 218 ± 4 | 97 ± 1 | 36 ± 4 | 0.78 ± 0.1 | 1.6 ± 0.04 | + + |

4+ = marked occurrence of atheromas in terms of number and extension
2+ + = about 50% of occurrence in controls
1+ = occurrence approximately equal to that in normal rabbits (2) Biological activity The aspects of biological activity determined were the anticoagulating activity (in accordance with USP) and the clarification activity on rats (Morton Grosman Method, J. Lab. and Clin. Med., March 1954, page 445). With regard to this latter determination, modifications were introduced in the present case to enable the effect to be expressed in international lipasemic units (ULI), in accordance with the UIB definition (International Biochemical Union), where one international unit (ULI) is equal to the activity which transforms the substrate at a speed of 1 micromole per minute.

The results of the biological activity aspects of FAPA are shown in Table II, in comparison with heparin and aorta extract.

TABLE II

|  | Heparin | Aorta Extract | FAPA |
|---|---|---|---|
| Anticoagulating Activity (USP/mg) | 135–148 | About 0.5 | 5–15 |
| Clarification activity (UL/l of plasma) at | 480 ± 100 | 15 ± 7 | 270 ± 80 |

TABLE II-continued

|  | Heparin | Aorta Extract | FAPA |
|---|---|---|---|
| a dose of 0.5 mg/kg | | | |

(3) Product Tolerance (a) Toxicity: FAPA proved to be well tolerated by rats, rabbits and guinea pigs treated either by parenteral administration or by oral administration with per diem doses of 200 mg/kg.

(b) Immunological tests: In guinea pigs treated with FAPA, immunological tests on antibody and anaphylaxis production gave no antibody or anaphylactogenic response.

(c) Vasokinetic investigations: no effect, either of histamine or adrenaline type, was noted even with doses of 50 mg/kg.

All of the aforesaid tests show that FAPA can be chosen as a drug for antiarteriosclerotic use as its effectiveness is of the order to magnitude of heparin, but without giving rise to the risks of haemorrhage typical of this latter substance.

Furthermore, the biological activity of FAPA is approximately ten times greater than that of total aorta extract, but without the immunoreactive side-effects, and thus with considerable advantage with regard to posology and the risk of sensitisations during therapy.

Some practical examples of preparation of the new arterial polysaccharide complex according to the invention are given hereinafter, in order to enable the process to be easily reproduced, but without in any way limiting it.

EXAMPLE 1

Calf aorta (50 kg.) were finely ground and homogenised in water (66 l.) After slowly heating the mass to 50° C., papain (0.6 kg.) were added, previously suspended in water (9 l.) containing sodium metabisulphite (10 g.).

The entire mass was heated to 65° C. and kept under these conditions for three hours, taking care that the pH did not descend below 6 by suitably adding alkali. After this time had passed, the mass was heated to 95° C. for 15 minutes.

After standing for 30 minutes, the mass was filtered through cloth with a precoat of filter earth.

Cetyltrimethylammonium chloride (0.6 kg.) dissolved in water (35 l.) was added to the filtrate.

After leaving overnight, the overlying liquid was syphoned off. The precipitate was collected by filtration and dissolved in water (25 l.) containing sodium chloride (3 kg.) by heating to 70° C. This solution was clarified by filtration. The filtrate was treated with an equal volume of acetone. The precipitate, namely the crude sodium salt of FAPA, was washed several times with 70% acetone and then dried. Crude sodium salt of FAPA (85 g.) was obtained in this manner.

This precipitate was washed in water (1500 ml), the pH of the mixture was adjusted to 8 and it was then treated with potassium permanganate (1.5 g.) and gradually heated to 90° C. This mixture was filtered to eliminate the precipitate formed and the pH of the filtrate was adjusted to 11 with sodium hydrate and kept at 70° C. for 10 hours.

After 10 hours, the liquid was cooled, its pH adjusted to 7 with hydrochloric acid, and filtered through a 0.8 micron membrane. The liquid obtained was treated with 2 volumes of ethyl alcohol.

After 2 hours of standing, the precipitate formed was collected by filtration and washed with 75% alcohol (500 ml). The precipitate was dissolved in water (800 ml) and concentrated until the residual alcohol was eliminated. The concentrate was filtered through a 0.2 micron membrane, and the clear filtrate was lyophilised.

In this manner 42 g of the sodium salt of FAPA was obtained, having the following characteristics:
uronic acid: 35%,
hexosamine: 30.5%,
—$SO_3Na$: 18.1%,
—nucleosides: 5.2%,
inorganic salts: 8% (mainly chlorides),
clarification activity: 210±20 ULI/l,
anticoagulation activity: 6 UL/mg

EXAMPLE 2

Pig aorta (50 kg.) was processed as in Example 1. Sodium salt of FAPA (36 g) was obtained with chemical-physical characteristics closely analogous to those given Example 1, including a clarification activity of 180±ULI/l.

EXAMPLE 3

Calf aorta (50 kg.) was lysised with ficin instead of papain, and the procedure of Example 1 was then followed. There was thus obtained 35 g of the sodium salt of FAPA with chemical-physical characteristics closely analogous to those given in Example 1, including a clarification activity of 280+40 ULI/l.

EXAMPLE 4

Calf aorta (50 kg.) was homogenized in water (150.1) and lysised with pancreatin (2 kg.) at pH 8 and 40° C. for 24 hours, in the presence of toluene as the bacteriostatic.

After filtering, the clear liquid was treated with 3 volumes of acetone. The precipitate obtained was hydrolysed with alkali at pH 11 and 70° C. for 15 hours. After filtering, the liquid was treated with cetylpiridinochloride (400 g) to afford the corresponding insoluble quaternary ammonium salt of FAPA. The precipitate was then dissolved in water (1500 ml.) containing calcium chloride (90 g). After filtering, the liquid was treated at pH 8 with potassium permanganate (1 g), heated to 90° C. and filtered. The filtrate was dialysed for 15 hours against a stream of water to eliminate the excess of salts, and then filtered through a 0.45 micron membrane and lyophilized. In this manner 35.5 of the calcium salt of FAPA was obtained, with chemical-physical characteristics closely analogous to those of the product of Example 1, including a clarification induction activity of 315±30 ULI/l.

What is claimed is:

1. An arterial polysaccharide complex of the formula:

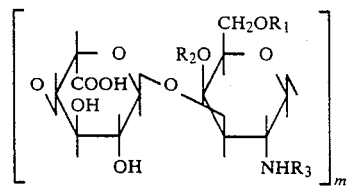

-continued

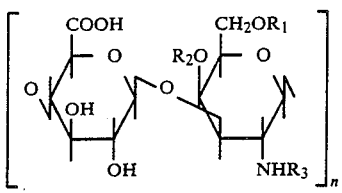

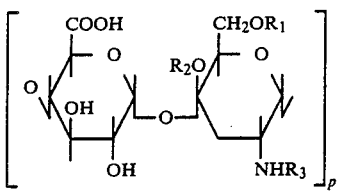

wherein $R_1$ and $R_2$ represent hydrogen, sulfur or acetyl, $R_3$ represents —$SO_3H$ or —CO—$CH_3$ and m, n and p are integers which define a molecular weight of 10,000 to 30,000 daltons for the polysaccharide chains and the nontoxic pharmacologically acceptable acid addition salts thereof.

2. A polysaccharide complex according to claim 1 consisting of hexosamine glycanmonosulphates derived from the aorta of young mammals, and having the following characteristics:
(a) on acid hydrolysis it liberates hexosamine and uronic acids in the molar ratio of approximately 1/1, together with variable quantities of nucleosides;
(b) electrophoretically, it separates into three anionic bands which can be seen with Alcian Blau and Toluidine Blue;
(c) it reacts with alkaline and alkaline earth metal bases to form salts soluble in water, whereas with the aliphatic ammonium ion it forms salts insoluble in water;
(d) its sodium salt is soluble to the extent of 2% in 50% ethyl alcohol, whereas its acid form is soluble to the extent of 2% in 70% ethyl alcohol;
(e) it reacts with Toluidine Blue to give a minimum metachromatic reaction;
(f) spectrophotometrically it shows a maximum at 260±nm; and
(g) it has a rotatory power on polarised light of −11° to −22°.

3. A therapeutic composition effective in treating arteriopathies which contains as the active ingredient an effective amount of the polysaccharide complex of claim 1 or claim 2 in combination with a therapeutically acceptable carrier.

4. A method for the treatment of arteriopathies which comprises administering to a host a therapeutically effective amount of the arterial polysaccharide complex of claim 1 or claim 2.

5. A polysaccharide complex according to claim 1 in the form of its alkali metal or alkaline earth metal salts.

6. A polysaccharide complex according to claim 1 in the form of its sodium salt.

7. A polysaccharide complex according to claim 1 in the form of its calcium salt.

* * * * *